United States Patent [19]

Lawrence

[11] Patent Number: 4,692,273

[45] Date of Patent: Sep. 8, 1987

[54] NOVEL GEL COMPOSITIONS, PROCESSES FOR MAKING SAME AND USES IN TRANSMITTING AND MEASURING ELECTRICAL IMPULSES

[75] Inventor: Katherine Lawrence, Trabuico Canyon, Calif.

[73] Assignee: Hewlett-Packard Company, Palo Alto, Calif.

[21] Appl. No.: 723,391

[22] Filed: Apr. 15, 1985

[51] Int. Cl.$^4$ ............................................. H01B 1/06
[52] U.S. Cl. ................................... 252/518; 252/500; 252/520; 252/315.3; 128/640
[58] Field of Search ............... 252/500, 518, 520, 316, 252/315.01, 315.1, 315.3; 128/641, 639, 640, 644; 524/176, 401, 55

[56] References Cited

U.S. PATENT DOCUMENTS

| | | | |
|---|---|---|---|
| 4,215,696 | 8/1980 | Brener et al. | 128/641 |
| 4,406,827 | 9/1983 | Carim | 252/518 |

Primary Examiner—Josephine L. Barr
Attorney, Agent, or Firm—E. J. Berry

[57] ABSTRACT

This invention comprises improved novel aqueous gel compositions, and devices and methods for preparation of such compositions. The invention also includes the uses of these novel compositions and devices made therefrom as linkages for transmitting and measuring electrical phenomena, and particularly for detecting and transmitting electrical impulses from mammalian skin to or through electrodes. Generally, the compositions of the invention contain critical and specific amounts of polyacrylamide, a titanium organic compound, specific and selected organic gums and at least one conductive salt.

11 Claims, No Drawings

NOVEL GEL COMPOSITIONS, PROCESSES FOR MAKING SAME AND USES IN TRANSMITTING AND MEASURING ELECTRICAL IMPULSES

FIELD OF THE INVENTION

This invention generally relates to measuring devices used to detect, measure, and record electrical phenomena on and within the mammalian body, particularly the human body, which devices, for their operation, require an electrical linkage to the body. More specifically, the invention includes the hydrogel compositions, processes for making, and methods for using same for disks and like devices especially adapted to transmit electrical impulses and function as an electrical linkage from the body to electrodes and to sensing and measuring devices as well as for use in situations where it is necessary to transmit effectively and accurately electrical energy into the mammalian body.

BACKGROUND OF THE INVENTION

Various substances and compositions have been used to establish electrical linkages with mammaliam (human) skin, but all those developed to date suffer from a number of disadvantages. Saline solutions are not neat in use and are prone to evaporate, thereby changing their concentration and leading to the introduction of errors and complication in electrical base line shifts. Furthermore, they are difficult to use as they must be kept in place by some other device, for instance a suction bulb which can result in raising welts on the skin of the patient. Conductive gels and creams have the advantage that they do not readily evaporate, but they are also far from neat to use and must be cleaned up after completion of measurements not only from the patient but from the equipment as well. Also the salt content of the adhering residue of such gels and creams cause the metal parts of the measuring equipment in contact with the residues to tarnish, oxidize, and ultimately fail. Moreover, since these creams and gels are rather fluid, as the mass of the gel moves or flows, the electronic monitoring equipment interprets this as electrical action and therefore reports it as such, to cause a defect known as motion artifact which is a nuisance in most cases and sometimes even leads to false findings. Pads or semisolid gels have been proposed to overcome these difficulties. For example U.S. Pat. No. 3,998,215 describes a gel pad which consists of an electronically conductive hydrogel and an electrode of a sensing device impregnated in a porous matrix or held within a cavity. This invention relies on a fibrous stiff carrier. However, this device suffers from a number of disadvantages. The pads tend to lose water through evaporation and have lower contactivity and higher impedance than do the creams and gels. Another attempt to resolve these problems if found in U.S. Pat. No. 4,125,110. Based on Karaya gum which is somewhat difficult to handle once wetted, as it tends to cake, the composition contains less than 3% water, nominally, and almost no salt, that is neither sodium chloride nor calcium chloride. Thus, its conductivity and ability to pass electrical signals and pulses is greatly impaired and it is less effective for the use intended.

Other U.S. patents of potential interest in connection with this invention are U.S. Pat. Nos. 3,993,049; 4,066,078; 4,215,696; 4,105,033; 3,743,613; 3,734,820; 3,833,518; 4,097,430; 3,301,723; 3,249,109; and 4,274,420.

According to the present invention, these problems are solved without a fiberous carrier and without having to resort either to low water and low salt content or to messy gels and creams which yield unavoidable residues.

SUMMARY OF THE INVENTION

An objective of the invention is to provide compositions for use in transmitting electrical impulses to and from mammalian skin and/or to detect, measure, and record electrical phenomena within the mammalian body, and more particularly within, to and from the human body.

It is a further objective to prepare these compositions and to use these specially adapted materials alone or in connection with electrodes or other devices to detect, measure, transmit, and record electrical impulses in connection with the human body.

It is another objective to provide compositions which avoid the disadvantages of the various compositions, methods and devices currently in use and/or known in the art.

Other objects will become apparent from the more detailed description of the invention set forth below.

DETAILED DESCRIPTION OF THE INVENTION

The present invention uses a conductive mixture containing at least two polymers, each of which contributes to the compostion of the gels and to the advantages of the invention as a contact composition. In a preferred embodiment of the invention, one of the polymers is a gum such as for instance, gum tragacanth, which absorbs and holds water, imparting a spongy quality. Other gums which have been used either alone or in combination with others include guar, xanthan, Karaya gums and carboxy methyl cellulose.

The other polymer is preferably polyacrylamide, (e.g. polyacrylamide 834A sold by American Cyanamid Corp.) which, according to the present invention, is cross-linked, turning the polyacrylamide into an elastic or elastomer-like material. A preferred crosslinking agent is a titanium containing organic compound such as titanium ammonium lactate, currently marketed by E. I. du Pont de Nemours & Company, Inc., under the Trademark name Tyzor LA. By altering the pH of the solution, the crosslinking agent reacts with the free carboxylic groups of the polyacrylamide to create a three-dimensional cage-like structure or "microstructural" sponge. Evidence for this bond has been found using a Hewlett-Packard UV/Visible spectophotometer. This crosslinking imparts great elasticity, strength and "memory" to the composition, with the advantages of having far better strength and greatly increased moisture retention capacity than do conventional gel pads which rely on only one gel or on a web for strength. Satisfactory results can be obtained with as little as 0.01% by weight of Tyzor LA, based on the final product, but amounts as high as 5% may be used as desired, depending on the degree of crosslinking and the exact consistency that is required in the final product.

The superior properties of the composition of the present invention are due, not only to its unexpected hygroscopic character, but also to the sponge-like behavior of the polymer network which is produced. Moreover, the gel remains pliable. This is aided in part by the addition of glycerol, sorbitol, propylene glycol alone or in combination or similar hygroscopic ingredients. It is probable that these polyols help to retain the sponginess of the galactomannan gums employed in the invention compositions.

The compositions have been successfully used in the defibrillation of dogs. For example Hewlett-Packard's Redux Past (Trademark product) which is generally accepted as the outstanding product for defibrillation coupling (electrical contact) medium was compared to the present invention for use in dogs weighing more than 25 kilograms, using Hewlett-Packard manufactured defibrillator. Resistances were in the order of 3 ohms, with fifty watt-second pulses, in both present invention and the Redux Paste. Highly satisfactory electrocardiograms were obtained even when the electrodes and/or cables were subjected to considerable motion and stress during their use to obtain the cardiogram.

The compositions of the invention have also been successfully used for obtaining electrocardiogram readings with human subjects. For this purpose, they have many advantages. The high water content and water retention, the ability to retain salt in the compositions, as well as pliability, strength and conformability to the skin all contribute to performance which was equal to, and in some characteristics superior to other materials known and used for the same or similar purposes. Also the unexpected combination of strength, conformity, and the ability to retain moisture allows these gels to be used in place of rigid gel cups without degradation of performance.

Currently, many electrodes are designed with integral gel cups. The purpose of these gel cups is to hold a fluid gel in place and to prevent excess gel from migrating or moving. The movement of the fluid gel during monitoring creates electrical interference called motion artifact. To eliminate this problem rigid gel cups are employed to contain the gel so that as the patient's limb moves, the cup moves sychronously and in the same direction. Although effective, the rigid gel cup adds cost to the electrode and certain complications including creating a "high profile". Moreover, it is possible that the cup can gouge the limb if the patient rolls over onto the electrode. Another approach to eliminating motion artifact due to gel "oozing" is to make an electrode which has an adhesive ring with a relatively larger diameter (e.g. 3 inches or more). In this kind of electrode the skin of the limb or body moves as a unit as the larger electrode adhesive ring captures and holds the electrolyte and skin. In laboratory experiments, it was found that electrodes of relatively smaller diameter (e.g. 1½ inches) showed appreciable motion artifact as compared to an electrode with the same diameter, but having a rigid gel cup.

Furthermore, a large diameter ring presents disadvantages from the standpoint of patient comfort, as more of the skin is covered which can lead, even in microporous adhesive rings, to rashes and skin irritation from allergic reaction or from keeping the skin under a dressing without adequate exposure to air. This is a problem especially with smaller patients. Smaller electrodes can, within certain narrow limits, be shifted without compromising the electrical readings to that over a period of days, the same skin is not continually covered by the adhesive ring, and thus the skin has some respite in prolonged monitoring. However, with the larger adhesive ring, the clinician does not have this latitude.

These problems can all be resolved if the rigid gel cup is replaced with compositions of the present invention. Although U.S. Pat. No. 4,125,110 teaches use of a solid gel, the gel is used as an adhesive medium and, since it covers a large area, and the gel employed has low salt and moisture contents, the resulting electrocardiograms made with it are not as good as those made with the electrode and compositions described herein nor are the skin impedances as low as with products of the present invention. For instance, a low profile electrode using the products and methods of the present invention gave outstanding electrocardiograms compared for example, to the Hewlett Packard 14445 and the 14240 gel cup electrodes.

The compositions, products, processes and methods of this invention can be used to provide a pathway both for sending and receiving impulses as well as for measurement, recording and all other purposes as are known in the art. These gel compositions of the present invention have uses other than as pathways for transmitting electrical impulses. Also, the materials need not be used with an electrode. Successful electrocardiograms have been carried out using the present invention gels in conjunction with Welsh cups and limb plates routinely used for diagnostic electrocardiographic measurements. Because of the cushioning effect of these gels there is no "suction welt", an undesirable side effect of the diagnostic tests. No saline residue is produced and the gels assist in forming a firm seal at the base of the suction cup, thus helping to retain the vacuum of the suction bulb.

The composition according to this invention, because of its strength can be used as a material of construction, affixed to materials normally used in disposable electrodes. This allows for a low profile electrode, not susceptible to motion artifact as above defined and is also less expensive since cost of the rigid gel cup has been eliminated.

In preparing the composition of the present invention, a relatively high total gum content is desirable. Amounts as low as 1.5% by weight are usable; however amounts of 5% up to about 10% by weight gum content gives better surface properties and moisture retention. As the percentage of gum increases in the composition the viscosity increases thus requiring more energy and more vigorous and prolonged stirring in order to avoid caking of the polymer, promote homogencity, and avoid "setting up" of the mixture, during the manufacturing cycle. Because of possible undesirable viscosity build-up, the gum is added to the water itself or, preferably to the aqueous polyacrylamide solution and after the part of the polyacrylamide is added. Since the polyol component enhances the pliability of the final product, the galactomannan gum can be dispersed in the anhydrous polyol in order to introduce it in disperison.

As with the galactomannan gum, the polyacrylamide component increases the viscosity of the solution as it hydrates. Best results are achieved by having polyacrylamide content of from about 0.5% up to about 2% by weight although as little as 0.1% and as much as 5% polyacrylamide can be used in compositions where variations in stiffness of fluidness are deemed desirable. Polyacrylamide hydrates more rapidly at elevated temperatures and at an alkaline pH.

Both sodium chloride and calcium chloride have been used successfully at the electrolytes. Other conductive salts can also be used. Use of electrolyte ranges from 1% to about 25% by weight although concentrations of 5% to 10% based on fianl product weight are found to have optimum properties. Additionally, calcium cholride is advantageous since it is hydroscopic and helps to retain and attract moisture. The salts also help to retard growth of bacteria and fungi in the gel.

The gums used can be any one of, or a combination of, the galactomannan gums or similar.

In general, they are naturally occurring materials. Particular gums found useful include gum tragacanth, guar gum, xanthan gum, and Karaya gum. Similar type gums of synthetic source can also be used. The presence of some gum tragacanth is preferred because of its bacterial inhibiting properties in the present invention. The gums are used in an amount of about 1.5% by weight up to about 12%.

It is also necessary to have present a cross-linking agent such as an organic titanate (as a salt). Those which have been found especially useful are the titanium ammonium lactates (Dupont Tyzor LA) for example, and other similarly constituted salts. An amount of from about 0.01% up to about 5% is preferred.

The presence of at least one polyol such as glycerol, propylene glycol, sorbitol, or polyol of similar properties is also advantageous. From 0.1% up to about 25% by weight can conveniently be employed.

If a white coloring agent is desired for the final product, titanium dioxide may advantageously be added at the mixing stage, in the amount of 1–2%, and preferably 1.3–1.5% by weight based on the weight of the final product.

If desired, a small amount of an emulsifier such as glycerol monostearate or cetyl alcohol may be added to the product to reduce skin impedance, but this is not necessary for achievement of the advantages of the invention.

ILLUSTRATIVE COMPOSITIONS

As an illustrative composition, the galactomannan gum and polyol (glycerol) mixture is prepared in one vessel, and polyacrylamide is added to water at slightly alkaline pH and a temperature of at least 130° F. up to about 160° F. Polyacrylamide is added under high sheer, and the mixture agitated, preferably with a turbine or similar mixture, until essentially all the polyacrylamide has fully hydrated. This condition is important as polyacrylamide that is not completely hydrated will not react properly in subsequent stages of preparation. Furthermore, it is not recommended that the temperature of the vessel exceed about 160° F. as higher temperature tend to affect adversely the chemical properties of the polyacrylamide. The electrolyte salt is then added to the polyacrylamide-water vessel. The contents of each vessel are then pumped into a manifold and through a set of Kenix (recirculation loop) in-line ribbon mixers. For efficient and complete mixing, the two solutions should be approximately similar in viscosity at the time of contact and mixing. Some of the galactomannan gum can be added to the polyacrylamide vessel if the viscosity of the mixture requires adjustment.

The Tyzor LA crosslinking agent (organic titanate salt) is injected into the Kenix loop ahead of a major part of the final Kenix mixer, but after the locations of the manifold and first mixer. Changing the pH activates the crosslinking agent and an elastomeric rope-like gel is created. This material can then for instance, be passed through a draft tube and by differential pressure, the viscosity can be measured. The material is then recycled if desired through the Kenix mixers and thereby viscosity and other properties more tightly controlled. A ten to one ratio of mixture in the resonance tank versus the amount of material in the feed has been found to produce the best results.

Material removed from this production line can either be air dried or dried with the assistance of heat. However, care should be taken not to dry the material too quickly since apparently delayed or latent reactions continue to take place throughout the twenty-four hour period following completion of manufacture. One additional advantage of the present invention is that iso-propyl alcohol or ethanol can also be added to the product. These low molecular weight hydroxy materials greatly aid in reduction of skin impedance and in lowering the surface tension of the skin. Moreover, they aid in carrying salts from the gel mass to the skin and this effect has proven very effective to defibrillator experiments. Up to 20% by weight of alcohol can be added. Moreoever, the present invention compositions will retain the alcohol over many weeks, even without packaging. As little as 0.1% by weight is effective.

EXAMPLES OF THE INVENTION

The invention is illustrated in greater and more detail by the following Examples although it is not intended to limit the invention compositions, processes for their preparation, and their uses specifically thereto. All parts are by weight unless otherwise specified.

EXAMPLE 1

A solution containing ten percent calcium chloride dihydrate was prepared using filtered water. This solution was heated to about 145° F. and was made alkaline with a small amount of sodium hydroxide. A portion of this solution equivalent to 741.4 parts in the final mix was used. Using vigorous agitation, 2.70 parts of commercial polyacrylamide (834A) (a product of American Cyanamid Corp.) was added to this mixture. The mixture was stirred until the polyacrylamide had fully hydrated. Then 67.4 parts of gum tragacanth, dispersed in 108 parts of 99.5% glycerol was added. After the two polymers had interacted, the mixture was acidified to a pH of about 4.5 using methyl purple as an indicator. As a separate mixture, 37 parts of a lactic acid titanium chelate ammonium salt (Du Pont) (Tyzor LA) were added to 213 parts water. To the initial mixture of interacted polymers, 16 parts of this mixture were added. The resulting total mixture was made alkaline with sodium hydroxide, allowed to cool, and spread into sheets to dry. It dried with a weight loss of about 20%.

EXAMPLE 2

This Example was carried out in a manner identical to that of Example #1 using 70 parts of 99.5% glycerol. Otherwise everything else was carried out in the same manner except that after the solution was made alkaline following the Tyzor LA addition, 38 parts ethanol were added to the mixture. The processing and preparatory steps following this step were essentially the same as that for Example #1. The resulting product retained the ethanol for many weeks. This superior ability to hold the ethanol is an unusual and unexpected advantage of the compositions.

EXAMPLE 3

To a solution of 160 parts sodium chloride in 800 parts water at 155° F. was added 24 parts of polyacrylamide 834A dispersed in 50 parts sorbitol. A dispersion of 5 parts guar gum in 20 parts of glycerol was thoroughly mixed into 55 parts by volume of the above solution. This solution was acidified to about a pH of 4.5 and 0.9 grams of Tyzor LA was added. Once completely dispersed, the product was made alkaline with a few drops of sodium hydroxide solution. The mixture was dried as gel sheets.

It has also been found possible to use Karaya gum as a replacement for part or all of the guar gum, or gum tragacanth in these compositions.

EXAMPLE 4

To a solution of 3.6 parts of sodium chloride in 16.7 parts of water, with stirring, was added a dispersion of 0.13 parts of xanthan gum in about 3.7 parts of glycerol. After dissolution was complete, a dispersion of 0.57 part of polyacrylamide 834A in 3.0 parts of glycerol was dissolved by stirring at a temperature below 120° F. A dispersion of 2.2 parts of guar gum in 8.3 parts of glycerol was then added with stirring, followed by 0.50 part of titanium dioxide, 0.1 part of Ottasept, and 0.4 part of Tyzor LA. The mixture rapidly developed the desired gel viscosity.

EXAMPLE 5

Samples of the flexible gels prepared according to the preceeding Examples 1, 2, 3 and 4 were cut into disk shapes and made into electrodes without using rigid gel cups. These disks were used to produce electrocardiograms. The resulting electrocardiograms were equal to, and in some instances, superior to those obtained using electrodes with rigid gel cups both when at rest and while being subjected to vigorous tugging and moving of the electrode and connecting cables. It was found, for instance, that the performance of 3 M electrodes was much improved, by as much as 25% efficiency, when the conventional gel-sponge was replaced by the gel prepared as described herein. In all cases in carrying out the tests, the adhesive ring diameter was nominally about one and a half inches. Both dogs and human patients were used in these test experiments.

What is claimed is:

1. An aqueous gel specially adapted for transmitting electrical impulses in connection with mammalian skin which comprises about 0.1% by weight of an organic titanate, about 1.5% up to about 10% by weight of at least one galactomannan gum, and a small but effective amount of from about 1% up to about 25% by weight of a conductive salt.

2. A gel according to claim 1 which is specially adapted for transmitting electrical impulses from human skin to an electrode.

3. A gel according to claim 1 or 2 which additionally contains from about 0.1% up to about 25% by weight of at least one polyol.

4. A gel according to claims 1, or 2 which additionally contains from about 0.1% up to about 20% by weight of a low molecular weight alcohol.

5. A gel according to claim 1 in which the galactomannan gum is gum tragacanth.

6. A gel according to claim 1 in which the galactomannan gum is guar gum.

7. A gel according to claim 1 in which the galactomannan gum is xanthan gum.

8. A gel according to claims 1, or 2 which contains from about 0.1% up to about 25% by weight of glycerol.

9. A gel according to claims 1, or 2 which contains from about 0.1% up to about 25% by weight of sorbitol.

10. A gel according to claims 1, or 2 which contains from about 0.1% up to about 20% by weight of ethanol.

11. A gel according to claims 1, or 2 in which the organic titanate is titanium ammonium lactate.

* * * * *